(12) United States Patent
Weiner et al.

(10) Patent No.: US 8,389,706 B2
(45) Date of Patent: Mar. 5, 2013

(54) VACCINES FOR HUMAN PAPILLOMA VIRUS AND METHODS FOR USING THE SAME

(75) Inventors: David B Weiner, Merion, PA (US); Jian Yan, Havertown, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 321 days.

(21) Appl. No.: 12/691,588

(22) Filed: Jan. 21, 2010

(65) Prior Publication Data
US 2010/0189730 A1   Jul. 29, 2010

Related U.S. Application Data

(60) Provisional application No. 61/146,942, filed on Jan. 23, 2009.

(51) Int. Cl.
- C07H 21/04 (2006.01)
- C12Q 1/00 (2006.01)
- C12Q 1/70 (2006.01)
- C12Q 1/68 (2006.01)
- C12P 19/34 (2006.01)
- C12N 7/00 (2006.01)
- C12N 7/01 (2006.01)

(52) U.S. Cl. ............... 536/23.72; 536/23.1; 536/23.4; 536/23.7; 435/4; 435/5; 435/6.1; 435/91.32; 435/91.33; 435/235.1

(58) Field of Classification Search .................. None
See application file for complete search history.

(56) References Cited

U.S. PATENT DOCUMENTS

| | | |
|---|---|---|
| 4,510,245 A | 4/1985 | Cousens et al. |
| 4,722,848 A | 2/1988 | Paoletti et al. |
| 4,790,987 A | 12/1988 | Compans et al. |
| 4,797,368 A | 1/1989 | Carter et al. |
| 4,920,209 A | 4/1990 | Davis et al. |
| 4,945,050 A | 7/1990 | Sanford et al. |
| 5,017,487 A | 5/1991 | Stunnenberg et al. |
| 5,036,006 A | 7/1991 | Sanford et al. |
| 5,077,044 A | 12/1991 | Stocker |
| 5,110,587 A | 5/1992 | Paoletti et al. |
| 5,112,749 A | 5/1992 | Brey, III et al. |
| 5,174,993 A | 12/1992 | Paoletti |
| 5,223,424 A | 6/1993 | Cochran et al. |
| 5,225,336 A | 7/1993 | Paoletti |
| 5,240,703 A | 8/1993 | Cochran |
| 5,242,829 A | 9/1993 | Panicali et al. |
| 5,294,441 A | 3/1994 | Curtiss, III |
| 5,294,548 A | 3/1994 | McLinden et al. |
| 5,310,668 A | 5/1994 | Ellis et al. |
| 5,387,744 A | 2/1995 | Curtiss, III et al. |
| 5,389,368 A | 2/1995 | Gurtiss, III |
| 5,424,065 A | 6/1995 | Curtiss, III et al. |
| 5,451,499 A | 9/1995 | Cochran |
| 5,453,364 A | 9/1995 | Paoletti |
| 5,462,734 A | 10/1995 | Letchworth, III et al. |
| 5,470,734 A | 11/1995 | Sondermeijer et al. |
| 5,474,935 A | 12/1995 | Chatterjee et al. |
| 5,482,713 A | 1/1996 | Paoletti |
| 5,580,859 A | 12/1996 | Felgner et al. |
| 5,591,439 A | 1/1997 | Plotkin et al. |
| 5,593,972 A | 1/1997 | Weiner et al. |
| 5,643,579 A | 7/1997 | Hung et al. |
| 5,650,309 A | 7/1997 | Wong-Staal et al. |
| 5,676,594 A | 10/1997 | Joosten |
| 5,698,202 A | 12/1997 | Ertl et al. |
| 5,703,055 A | 12/1997 | Felgner et al. |
| 5,739,118 A | 4/1998 | Carrano et al. |
| 5,817,637 A | 10/1998 | Weiner et al. |
| 5,830,876 A | 11/1998 | Weiner et al. |
| 5,955,088 A | 9/1999 | Ghiasi et al. |
| 5,962,428 A | 10/1999 | Carrano et al. |
| 5,981,505 A | 11/1999 | Weiner et al. |
| 6,034,298 A | 3/2000 | Lam et al. |
| 6,042,836 A | 3/2000 | Berman et al. |
| 6,156,319 A | 12/2000 | Cohen et al. |
| 6,589,529 B1 | 7/2003 | Choi et al. |
| 7,245,963 B2 | 7/2007 | Draghia-Akli et al. |
| 2005/0031638 A1 | 2/2005 | Dalemans et al. |
| 2005/0052630 A1 | 3/2005 | Smith et al. |

FOREIGN PATENT DOCUMENTS

| | | |
|---|---|---|
| WO | WO9416737 | 8/1994 |
| WO | WO9910375 | 3/1999 |
| WO | WO2007/119896 | 10/2007 |
| WO | WO 2007119896 A1 * | 10/2007 |
| WO | WO2007121894 | 11/2007 |
| WO | WO2008014521 | 1/2008 |

OTHER PUBLICATIONS

Yan et al. Cellular immunity induced by a novel HPV18 DNA vaccine encoding an E6/E7 fusion consensus protein in mice and rhesus macaques. Vaccine Sep. 19, 2008, vol. 26, Issue 40, pp. 5210-5215.*
Andre, S., et al,. "Increased immune response elicited by DNA vaccination with a synthetic gp120 sequence with optimized codon usage", J Virol, 1998, 72(2): 1497-503.
Deml, L., et al., "Multiple effects of codon usage optimization on expression and immunogenicity of DNA candidate vaccines encoding the human immunodeficiency virus type 1 Gag protein.", J Virol, 2001, 75(22): 10991-11001.
Laddy, D.J., et al., "Immunogenicity of novel consensus-based DNA vaccines against avian influenza."Vaccine, 2007, 25(16): 2984-2989.
Frelin, L., et al., "Codon optimization and mRNA amplification effectively enhances the immunogenicity of the hepatitis C virus nonstructural 3/4A gene." Gene Ther, 2004, 11(6): 522-533.
Mahdavi et al., "Vaccines Against Human Papillomavirus and Cervical Cancer: Promises and Challenges", The Oncologist, 2005, 10(7):528-538.
Yan, J. et al., "Induction of antitumor immunity in vivo following delivery of a novel HPV-16 DNA vaccine encoding an E6/E7 fusion antigen", Vaccine, 2009, 27:431-440.
Hirao, L. et al., "Combined effects of IL-12 and electroporation enhances the potency of DNA vaccination in macaques", Vaccine, 2008, 26:3112-3120.
Hirao, L. et al., "Intradermal/subcutaneous immunization by electroporation improves plasmid vaccine delivery and potency in pigs and rhesus macaques", Vaccine, 2007, 26:440-448.
Luckay, A. et al., "Effect of plasmid DNA vaccine design and in vivo electroporation on the resulting vaccine-specific immune responses in rhesus macaques", Journal of Virology, 2007, 81:5257-5269.

* cited by examiner

*Primary Examiner* — Louise Humphrey
(74) *Attorney, Agent, or Firm* — Pepper Hamilton, LLP (57) ABSTRACT

Improved anti-HPV immunogens and nucleic acid molecules that encode them are disclosed. Immunogens disclosed include those having consensus HPV 18 E6 and E7. Pharmaceutical composition, recombinant vaccines comprising and live attenuated vaccines are disclosed as well methods of inducing an immune response in an individual against HPV are disclosed.

40 Claims, 1 Drawing Sheet

SEQUENCE LISTING

<160> NUMBER OF SEQ ID NOS: 7

<210> SEQ ID NO 1
<211> LENGTH: 783
<212> TYPE: DNA
<213> ORGANISM: Artificial Sequence
<220> FEATURE:
<223> OTHER INFORMATION: HPV Consensus Sequence encoding E6 and E7

<400> SEQUENCE: 1

```
gccagattcg aggaccccac caggagcggc tacaagctgc ccgatctgtg taccgagctg      60
aacaccagcc tgcaggacat cgagatcacc tgtgtgtact gtaagaccgt gctggagctg     120
accgaggtgt tcgagaagga cctgttcgtg gtgtacaggg acagcatccc ccacgccgcc     180
tgccacaagt gtatcgactt ctacagccgg atccgggagc tgagacacta cagcgacagc     240
```

```
gtgtacggcg ataccctgga gaagctgacc aacaccggcc tgtacaacct gctgatccgg    300
tgcctgagat gccagaagcc cctgctgaga cacctgaacg agaagcggcg gttccacaac    360
atcgccggcc actacagagg ccagtgccac agctgctgta acagggccag gcaggagaga    420
ctgcagcgga gaagagagac caggtgaggg gcaggaagag aagaagccac ggccccaag    480 gccaccctgc aggatatcgt gctgcacctg gagccccaga tgagatccc cgtggatctg    540 ctgggccacg gccagctgtc cgacagcgag gaggagaacg acgagatcga cggcgtgaat    600
caccagcacc tgcctgccag aagagccgag cctcagaggc acaccatgct gtgtatgtgc    660
tgtaagtgtg aggcccggat cgaactggtg gtggagagca gcgccgacga cctgagagcc    720
ttccagcagc tgttcctgaa cacccctgagc ttcgtgtgtc cttggtgtgc cagccagcag    780
tga                                                                  783
```

`<210>` SEQ ID NO 2
`<211>` LENGTH: 260
`<212>` TYPE: PRT
`<213>` ORGANISM: Artificial Sequence
`<220>` FEATURE:
`<223>` OTHER INFORMATION: Consensus HPV peptide sequence with E6 and E7

`<400>` SEQUENCE: 2

```
Ala Arg Phe Glu Asp Pro Thr Arg Ser Gly Tyr Lys Leu Pro Asp Leu
1               5                   10                  15

Cys Thr Glu Leu Asn Thr Ser Leu Gln Asp Ile Glu Ile Thr Cys Val
            20                  25                  30

Tyr Cys Lys Thr Val Leu Glu Leu Thr Glu Val Phe Glu Lys Asp Leu
        35                  40                  45

Phe Val Val Tyr Arg Asp Ser Ile Pro His Ala Ala Cys His Lys Cys
    50                  55                  60

Ile Asp Phe Tyr Ser Arg Ile Arg Glu Leu Arg His Tyr Ser Asp Ser
65                  70                  75                  80

Val Tyr Gly Asp Thr Leu Glu Lys Leu Thr Asn Thr Gly Leu Tyr Asn
                85                  90                  95

Leu Leu Ile Arg Cys Leu Arg Cys Gln Lys Pro Leu Leu Arg His Leu
            100                 105                 110

Asn Glu Lys Arg Arg Phe His Asn Ile Ala Gly His Tyr Arg Gly Gln
        115                 120                 125

Cys His Ser Cys Cys Asn Arg Ala Arg Gln Glu Arg Leu Gln Arg Arg
    130                 135                 140

Arg Glu Thr Gln Val Arg Gly Arg Lys Arg Ser His Gly Pro Lys
145                 150                 155                 160

Ala Thr Leu Gln Asp Ile Val Leu His Leu Glu Pro Gln Asn Glu Ile
                165                 170                 175

Pro Val Asp Leu Leu Gly His Gly Gln Leu Ser Asp Ser Glu Glu Glu
            180                 185                 190

Asn Asp Glu Ile Asp Gly Val Asn His Gln His Leu Pro Ala Arg Arg
        195                 200                 205

Ala Glu Pro Gln Arg His Thr Met Leu Cys Met Cys Cys Lys Cys Glu
    210                 215                 220

Ala Arg Ile Glu Leu Val Val Glu Ser Ser Ala Asp Asp Leu Arg Ala
225                 230                 235                 240

Phe Gln Gln Leu Phe Leu Asn Thr Leu Ser Phe Val Cys Pro Trp Cys
                245                 250                 255

Ala Ser Gln Gln
```

<210> SEQ ID NO 3
<211> LENGTH: 54
<212> TYPE: DNA
<213> ORGANISM: Artificial Sequence
<220> FEATURE:
<223> OTHER INFORMATION: IgE Leader DNA sequence

<400> SEQUENCE: 3
atggactgga cctggatcct gttcctggtg ccgctgcca cacgggtgca cagc         54

<210> SEQ ID NO 4
<211> LENGTH: 18
<212> TYPE: PRT
<213> ORGANISM: Artificial Sequence
<220> FEATURE:
<223> OTHER INFORMATION: IgE leader peptide sequence

<400> SEQUENCE: 4

Met Asp Trp Thr Trp Ile Leu Phe Leu Val Ala Ala Ala Thr Arg Val
1               5                   10                  15

His Ser

<210> SEQ ID NO 5
<211> LENGTH: 837
<212> TYPE: DNA
<213> ORGANISM: Artificial Sequence
<220> FEATURE:
<223> OTHER INFORMATION: Consensus HPV Nucleic Acid Sequence Transgene
      including IgE

<400> SEQUENCE: 5
atggactgga cctggatcct gttcctggtg ccgctgcca cacgggtgca cagcgccaga         60
ttcgaggacc ccaccaggag cggctacaag ctgcccgatc tgtgtaccga gctgaacacc        120
agcctgcagg acatcgagat cacctgtgtg tactgtaaga ccgtgctgga gctgaccgag        180
gtgttcgaga aggacctgtt cgtggtgtac aggacagca tccccacgc cgcctgccac          240 aagtgtatcg acttctacag ccggatccgg gagctgagac actacagcga cagcgtgtac        300
ggcgataccc tggagaagct gaccaacacc ggcctgtaca acctgctgat ccggtgcctg        360
agatgccaga agccctgct gagacacctg aacgagaagc ggcggttcca caacatcgcc         420
ggccactaca gaggccagtg ccacagctgc tgtaacaggg ccaggcagga gagactgcag        480
cggagaagag agacccaggt gaggggcagg aagagaagaa gccacggccc caaggccacc        540
ctgcaggata tcgtgctgca cctggagccc cagaatgaga tccccgtgga tctgctgggc        600
cacggccagc tgtccgacag cgaggaggag acgacgaga tcgacggcgt gaatcaccag         660
cacctgcctg ccagaagagc cgagcctcag aggcacacca tgctgtgtat gtgctgtaag        720
tgtgaggccc ggatcgaact ggtggtggag agcagcgccg acgacctgag agccttccag        780
cagctgttcc tgaacacccct gagcttcgtg tgtccttggt gtgccagcca gcagtga          837

<210> SEQ ID NO 6
<211> LENGTH: 278
<212> TYPE: PRT
<213> ORGANISM: Artificial Sequence
<220> FEATURE:
<223> OTHER INFORMATION: Consensus HPV Protein Sequence with IgE leader
      peptide

<400> SEQUENCE: 6

Met Asp Trp Thr Trp Ile Leu Phe Leu Val Ala Ala Ala Thr Arg Val

```
              1               5              10              15
His Ser Ala Arg Phe Glu Asp Pro Thr Arg Ser Gly Tyr Lys Leu Pro
                20                  25                  30

Asp Leu Cys Thr Glu Leu Asn Thr Ser Leu Gln Asp Ile Glu Ile Thr
            35                  40                  45

Cys Val Tyr Cys Lys Thr Val Leu Glu Leu Thr Glu Val Phe Glu Lys
        50                  55                  60

Asp Leu Phe Val Val Tyr Arg Asp Ser Ile Pro His Ala Ala Cys His
65                  70                  75                  80

Lys Cys Ile Asp Phe Tyr Ser Arg Ile Arg Glu Leu Arg His Tyr Ser
                85                  90                  95

Asp Ser Val Tyr Gly Asp Thr Leu Glu Lys Leu Thr Asn Thr Gly Leu
            100                 105                 110

Tyr Asn Leu Leu Ile Arg Cys Leu Arg Cys Gln Lys Pro Leu Leu Arg
        115                 120                 125

His Leu Asn Glu Lys Arg Arg Phe His Asn Ile Ala Gly His Tyr Arg
130                 135                 140

Gly Gln Cys His Ser Cys Cys Asn Arg Ala Arg Gln Glu Arg Leu Gln
145                 150                 155                 160

Arg Arg Arg Glu Thr Gln Val Arg Gly Arg Lys Arg Arg Ser His Gly
                165                 170                 175

Pro Lys Ala Thr Leu Gln Asp Ile Val Leu His Leu Glu Pro Gln Asn
            180                 185                 190

Glu Ile Pro Val Asp Leu Leu Gly His Gly Gln Leu Ser Asp Ser Glu
        195                 200                 205

Glu Glu Asn Asp Glu Ile Asp Gly Val Asn His Gln His Leu Pro Ala
210                 215                 220

Arg Arg Ala Glu Pro Gln Arg His Thr Met Leu Cys Met Cys Cys Lys
225                 230                 235                 240

Cys Glu Ala Arg Ile Glu Leu Val Val Glu Ser Ser Ala Asp Asp Leu
                245                 250                 255

Arg Ala Phe Gln Gln Leu Phe Leu Asn Thr Leu Ser Phe Val Cys Pro
            260                 265                 270

Trp Cys Ala Ser Gln Gln
        275
```

<210> SEQ ID NO 7
<211> LENGTH: 3824
<212> TYPE: DNA
<213> ORGANISM: Artificial Sequence
<220> FEATURE:
<223> OTHER INFORMATION: pGX3002 plasmid with consensus and IgE leader

<400> SEQUENCE: 7

```
gctgcttcgc gatgtacggg ccagatatac gcgttgacat tgattattga ctagttatta    60
atagtaatca attacggggt cattagttca tagcccatat atggagttcc gcgttacata   120
acttacggta atggcccgc ctggctgacc gcccaacgac ccccgcccat tgacgtcaat   180
aatgacgtat gttcccatag taacgccaat agggactttc cattgacgtc aatgggtgga   240
gtatttacgg taaactgccc acttggcagt acatcaagtg tatcatatgc caagtacgcc   300
ccctattgac gtcaatgacg gtaaatggcc cgcctggcat tatgcccagt acatgacctt   360
atgggacttt cctacttggc agtacatcta cgtattagtc atcgctatta ccatggtgat   420
gcggttttgg cagtacatca atgggcgtgg atagcggttt gactcacggg gatttccaag   480
tctccacccc attgacgtca atgggagttt gttttggcac caaaatcaac gggactttcc   540
```

```
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttggt    720
accgagctcg gatccactag tccagtgtgg tggaattcgc caccatggac tggacctgga    780
tcctgttcct ggtggccgct gccacacggg tgcacagcgc cagattcgag accccacca    840
ggagcggcta caagctgccc gatctgtgta ccgagctgaa caccagcctg caggacatcg    900
agatcacctg tgtgtactgt aagaccgtgc tggagctgac cgaggtgttc gagaaggacc    960
tgttcgtggt gtacagggac agcatccccc acgccgcctg ccacaagtgt atcgacttct    1020
acagccggat ccgggagctg agacactaca gcgacagcgt gtacggcgat accctggaga    1080
agctgaccaa caccggcctg tacaacctgc tgatccggtg cctgagatgc agaagccccc    1140
tgctgagaca cctgaacgag aagcggcggt ccacaacat cgccggccac tacagaggcc    1200
agtgccacag ctgctgtaac agggccaggc aggagagact gcagcggaga agagagaccc    1260
aggtgagggg caggaagaga agaagccacg gccccaaggc caccctgcag gatatcgtgc    1320
tgcacctgga gccccagaat gagatccccg tggatctgct gggccacggc cagctgtccg    1380
acagcgagga ggagaacgac gagatcgacg gcgtgaatca ccagcacctg cctgccagaa    1440
gagccgagcc tcagaggcac accatgctgt gtatgtgctg taagtgtgag gcccggatcg    1500
aactggtggt ggagagcagc gccgacgacc tgagagcctt ccagcagctg ttcctgaaca    1560
ccctgagctt cgtgtgtcct tggtgtgcca gccagcagtg atgagcggcc gctcgagtct    1620
agagggcccg tttaaacccg ctgatcagcc tcgactgtgc cttctagttg ccagccatct    1680
gttgtttgcc cctcccccgt gccttccttg accctggaag gtgccactcc cactgtcctt    1740
tcctaataaa atgaggaaat tgcatcgcat tgtctgagta ggtgtcattc tattctgggg    1800
ggtggggtgg ggcaggacag caaggggag gattgggaag acaatagcag gcatgctggg    1860
gatgcggtgg gctctatggc ttctactggg cggttttatg gacagcaagc gaaccggaat    1920
tgccagctgg ggcgccctct ggtaaggttg gaagccctg caaagtaaac tggatggctt    1980
tcttgccgcc aaggatctga tggcgcaggg gatcaagctc tgatcaagag acaggatgag    2040
gatcgtttcg catgattgaa caagatggat tgcacgcagg ttctccggcc gcttgggtgg    2100
agaggctatt cggctatgac tgggcacaac agacaatcgg ctgctctgat gccgccgtgt    2160
tccggctgtc agcgcagggg cgcccggttc tttttgtcaa gaccgacctg tccggtgccc    2220
tgaatgaact gcaagacgag gcagcgcggc tatcgtggct ggccacgacg ggcgttcctt    2280
gcgcagctgt gctcgacgtt gtcactgaag cgggaaggga ctggctgcta ttgggcgaag    2340
tgccggggca ggatctcctg tcatctcacc ttgctcctgc cgagaaagta tccatcatgg    2400
ctgatgcaat gcggcggctg catacgcttg atccggctac ctgcccattc gaccaccaag    2460
cgaaacatcg catcgagcga gcacgtactc ggatggaagc cggtcttgtc gatcaggatg    2520
atctggacga agagcatcag gggctcgcgc cagccgaact gttcgccagg ctcaaggcga    2580
gcatgcccga cggcgaggat ctcgtcgtga cccatggcga tgcctgcttg ccgaatatca    2640
tggtggaaaa tggccgcttt tctggattca tcgactgtgg ccggctgggt gtggcggacc    2700
gctatcagga catagcgttg ctacccgtg atattgctga agagcttggc ggcgaatggg    2760
ctgaccgctt cctcgtgctt tacggtatcg ccgctcccga ttcgcagcgc atcgccttct    2820
atcgccttct tgacgagttc ttctgaatta ttaacgctta caatttcctg atgcggtatt    2880
ttctccttac gcatctgtgc ggtatttcac accgcatcag gtggcacttt tcggggaaat    2940
```

```
gtgcgcggaa ccoctatttg tttattttto taaatacatt caaatatgta tccgctcatg    3000
agacaataac cctgataaat gcttcaataa tagcacgtgc taaaacttca ttttttaattt   3060 aaaaggatct aggtgaagat ccttttttgat aatctcatga ccaaaatccc ttaacgtgag   3120
ttttcgttcc actgagcgtc agacccgta gaaaagatca aaggatcttc ttgagatcct    3180 tttttctgc gcgtaatctg ctgcttgcaa acaaaaaaac caccgctacc agcggtggtt    3240
tgtttgccgg atcaagagct accaactctt tttccgaagg taactggctt cagcagagcg   3300
cagataccaa atactgttct tctagtgtag ccgtagttag gccaccactt caagaactct    3360
gtagcaccgc ctacatacct cgctctgcta atcctgttca cagtggctgc tgccagtggc   3420
gataagtcgt gtcttaccgg gttggactca agacgatagt taccggataa ggcgcagcgg   3480
tcgggctgaa cggggggttc gtgcacacag cccagcttgg agcgaacgac ctacaccgaa   3540
ctgagatacc tacagcgtga gctatgagaa agcgccacgc ttcccgaagg gagaaaggcg   3600
gacaggtatc cggtaagcgg cagggtcgga acaggagagc gcacgaggga gcttccaggg   3660
ggaaacgcct ggtatcttta tagtcctgtc gggtttcgcc acctctgact tgagcgtcga   3720
tttttgtgat gctcgtcagg ggggcggagc ctatggaaaa acgccagcaa cgcggccttt   3780
ttacggttcc tggccttttg ctggccttt  gctcacatgt tctt                    3824
```

VACCINES FOR HUMAN PAPILLOMA VIRUS AND METHODS FOR USING THE SAME

CROSS REFERENCE TO RELATED APPLICATIONS

This application claims priority to U.S. Provisional Application No. 61/146,942 filed Jan. 23, 2009, the disclosure of which is incorporated herein by reference.

FIELD OF THE INVENTION

The present invention relates to improved human papillomavirus (HPV) vaccines, improved methods for inducing immune responses, and for prophylactically and/or therapeutically immunizing individuals against HPV.

BACKGROUND OF THE INVENTION

Papillomavirus are small DNA viruses that comprise up to seven early genes and two late genes. Generally, papilloma virus early genes are designated E1-E7, and papilloma virus late genes are designated L1 and L2. Several species of animals can be infected by members of the papillomavirus family.

Human Papillomavirus (HPV) infection is common and can be transmitted sexually. HPV have been differentiated into 56 or more types based upon DNA sequence homology. HPV types 16 and 18, which cause epithelial dysplasia and other lesions, are often associated with an increased risk of cancer, particularly in situ and invasive carcinomas of the cervix, vagina, vulva and anal canal.

DNA vaccines have many conceptual advantages over more traditional vaccination methods, such as live attenuated viruses and recombinant protein-based vaccines. DNA vaccines are safe, stable, easily produced, and well tolerated in humans with preclinical trials indicating little evidence of plasmid integration [Martin, T., et al., Plasmid DNA malaria vaccine: the potential for genomic integration after intramuscular injection. Hum Gene Ther, 1999. 10(5): p. 759-68; Nichols, W. W., et al., Potential DNA vaccine integration into host cell genome Ann NY Acad Sci, 1995. 772: p. 30-9]. In addition, DNA vaccines are well suited for repeated administration due to the fact that efficacy of the vaccine is not influenced by pre-existing antibody titers to the vector [Chattergoon, M., J. Boyer, and D. B. Weiner, Genetic immunization: a new era in vaccines and immune therapeutics. FASEB J, 1997. 11(10): p. 753-63]. However, one major obstacle for the clinical adoption of DNA vaccines has been a decrease in the platforms immunogenicity when moving to larger animals [Liu, M. A. and J. B. Ulmer, Human clinical trials of plasmid DNA vaccines. Adv Genet, 2005. 55: p. 25-40]. Recent technological advances in the engineering of DNA vaccine immunogen, such has codon optimization, RNA optimization and the addition of immunoglobulin leader sequences have improved expression and immunogenicity of DNA vaccines [Andre, S., et al., Increased immune response elicited by DNA vaccination with a synthetic gp120 sequence with optimized codon usage. J Virol, 1998. 72(2): p. 1497-503; Deml, L., et al., Multiple effects of codon usage optimization on expression and immunogenicity of DNA candidate vaccines encoding the human immunodeficiency virus type 1 Gag protein. J Virol, 2001. 75(22): p. 10991-1001; Laddy, D. J., et al., Immunogenicity of novel consensus-based DNA vaccines against avian influenza. Vaccine, 2007. 25(16): p. 2984-9; Frelin, L., et al., Codon optimization and mRNA amplification effectively enhances the immunogenicity of the hepatitis C virus nonstructural 3/4A gene. Gene Ther, 2004. 11(6): p. 522-33], as well as, recently developed technology in plasmid delivery systems such as electroporation [Hirao, L. A., et al., Intradermal/subcutaneous immunization by electroporation improves plasmid vaccine delivery and potency in pigs and rhesus macaques. Vaccine, 2008. 26(3): p. 440-8; Luckay, A., et al., Effect of plasmid DNA vaccine design and in vivo electroporation on the resulting vaccine-specific immune responses in rhesus macaques. J Virol, 2007. 81(10): p. 5257-69; Ahlen, G., et al., In vivo electroporation enhances the immunogenicity of hepatitis C virus nonstructural 3/4A DNA by increased local DNA uptake, protein expression, inflammation, and infiltration of CD3+ T cells. J Immunol, 2007. 179(7): p. 4741-53]. In addition, studies have suggested that the use of consensus immunogens may be able to increase the breadth of the cellular immune response as compared to native antigens alone [Yan., J., et al., Enhanced cellular immune responses elicited by an engineered HIV-1 subtype B consensus-based envelope DNA vaccine. Mol Ther, 2007. 15(2): p. 411-21; Rolland, M., et al., Reconstruction and function of ancestral center-of-tree human immunodeficiency virus type 1 proteins. J Virol, 2007. 81(16): p. 8507-14].

There remains a need for improved vaccines and methods for preventing and treating HPV infection.

SUMMARY OF THE INVENTION

Proteins comprising a consensus HPV Type 18 (HPV 18) E6 and E7 amino acid sequence, and nucleic acid molecules comprising nucleotide sequences encoding such proteins are provided. These nucleic acid constructs and proteins encoded thereby provide improved immunogenic targets against which an anti-HPV immune response can be generated.

Constructs which encode such proteins, vaccines which comprise such proteins, vaccines which comprise nucleic acid molecules that encode such proteins, and methods of inducing anti-HPV immune responses are also provided.

Aspects of the invention include nucleic acid molecules comprising a nucleotide sequence selected from the group consisting of: SEQ ID NO:1; fragments of SEQ ID NO:1; sequences having at least 90% homology to SEQ ID NO:1; fragments of sequences having at least 90% homology to SEQ ID NO:1; SEQ ID NO:5; fragments of SEQ ID NO:5 including HPV coding sequences; sequences having at least 90% homology to SEQ ID NO:5; and fragments of sequences having at least 90% homology to SEQ ID NO:5 including HPV coding sequences; SEQ ID NO:7; fragments of SEQ ID NO:7 including HPV coding sequences; sequences having at least 90% homology to SEQ ID NO:7; and fragments of sequences having at least 90% homology to SEQ ID NO:7 including HPV coding sequences.

The present invention relates to nucleic acid molecules comprising a nucleotide sequence selected from the group consisting of: nucleotide sequences that encode SEQ ID NO:2; nucleotide sequences that encode an amino acid sequences having at least 90% homology to SEQ ID NO:2; nucleotide sequences that encode fragments of SEQ ID NO:2; nucleotide sequences that encode an amino acid sequences having at least 90% homology to fragments of SEQ ID NO:2; nucleotide sequences that encode SEQ ID NO:6; nucleotide sequences that encode fragments of SEQ ID NO:6 including HPV sequences; nucleotide sequences that encode an amino acid sequences having at least 90% homology to SEQ ID NO:6 including HPV sequences; and nucleotide sequences that encode an amino acid sequences having at least 90% homology to fragments of SEQ ID NO:6 including HPV sequences.

The present invention further provides pharmaceutical compositions comprising such nucleic acid molecules and their use in methods of inducing an immune response in an individual against HPV that comprise administering to an individual a composition comprising such nucleic acid molecules.

The present invention further provides recombinant vaccine comprising such nucleic acid molecules and their use in methods of inducing an immune response in an individual against HPV that comprise administering to an individual such a recombinant vaccine.

The present invention further provides live attenuated pathogens comprising such nucleic acid molecules and their use in methods of inducing an immune response in an individual against HPV that comprise administering to an individual such live attenuated pathogens.

The present invention further provides proteins comprising amino acid sequences selected from the group consisting of: SEQ ID NO:2, sequences having at least 90% homology to SEQ ID NO:2; fragments of SEQ ID NO:2; fragments of sequences having at least 90% homology to SEQ ID NO:2, SEQ ID NO:6, sequences having at least 90% homology to SEQ ID NO:6; fragments of SEQ ID NO:6; and fragments of sequences having at least 90% homology to SEQ ID NO:6.

The present invention further provides pharmaceutical compositions comprising such proteins and their use in methods of inducing an immune response in an individual against HPV that comprise administering to an individual a composition comprising such proteins.

The present invention further provides recombinant vaccines comprising such proteins and their use in methods of inducing an immune response in an individual against HPV that comprise administering to an individual such a recombinant vaccine.

The present invention further provides live attenuated pathogens comprising such proteins and their use in methods of inducing an immune response in an individual against HPV that comprise administering to an individual such live attenuated pathogens.

DETAILED DESCRIPTION OF PREFERRED EMBODIMENTS

As used herein, the phrase "stringent hybridization conditions" or "stringent conditions" refers to conditions under which a nucleic acid molecule will hybridize another nucleic acid molecule, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present in excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g. 10 to 50 nucleotides) and at least about 60° C. for longer probes, primers or oligonucleotides. Stringent conditions may also be achieved with the addition of destabilizing agents, such as formamide.

Sequence homology for nucleotides and amino acids may be determined using FASTA, BLAST and Gapped BLAST (Altschul et al., Nuc. Acids Res., 1997, 25, 3389, which is incorporated herein by reference in its entirety) and PAUP* 4.0b10 software (D. L. Swofford, Sinauer Associates, Massachusetts). "Percentage of similarity" is calculated using PAUP* 4.0b10 software (D. L. Swofford, Sinauer Associates, Massachusetts). The average similarity of the consensus sequence is calculated compared to all sequences in the phylogenic tree.

Briefly, the BLAST algorithm, which stands for Basic Local Alignment Search Tool is suitable for determining sequence similarity (Altschul et al., J. Mol. Biol., 1990, 215, 403-410, which is incorporated herein by reference in its entirety). Software for performing BLAST analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The Blast algorithm parameters W, T and X determine the sensitivity and speed of the alignment. The Blast program uses as defaults a word length (W) of 11, the BLOSUM62 scoring matrix (see Henikoff et al., Proc. Natl. Acad. Sci. USA, 1992, 89, 10915-10919, which is incorporated herein by reference in its entirety) alignments (B) of 50, expectation (E) of 10, M=5, N=4, and a comparison of both strands. The BLAST algorithm (Karlin et al., Proc. Natl. Acad. Sci. USA, 1993, 90, 5873-5787, which is incorporated herein by reference in its entirety) and Gapped BLAST perform a statistical analysis of the similarity between two sequences. One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about 1, preferably less than about 0.1, more preferably less than about 0.01, and most preferably less than about 0.001.

As used herein, the term "genetic construct" refers to the DNA or RNA molecules that comprise a nucleotide sequence which encodes protein. The coding sequence includes initiation and termination signals operably linked to regulatory elements including a promoter and polyadenylation signal capable of directing expression in the cells of the individual to whom the nucleic acid molecule is administered.

As used herein, the term "expressible form" refers to gene constructs that contain the necessary regulatory elements operable linked to a coding sequence that encodes a protein such that when present in the cell of the individual, the coding sequence will be expressed.

Improved vaccine are disclosed which arise from a multi-phase strategy to enhance cellular immune responses induced by immunogens. Modified consensus sequences were generated. Genetic modifications including codon optimization, RNA optimization, and the addition of a high efficient immunoglobin leader sequence are also disclosed. The novel construct has been designed to elicit stronger and broader cellular immune responses than a corresponding codon optimized immunogens.

The improved HPV vaccines are based upon proteins and genetic constructs that encode proteins with epitopes that make them particularly effective as immunogens against which anti-HPV can be induced. Accordingly, vaccines may induce a therapeutic or prophylactic immune response. In some embodiments, the means to deliver the immunogen is a DNA vaccine, a recombinant vaccine, a protein subunit vaccine, a composition comprising the immunogen, an attenuated vaccine or a killed vaccine. In some embodiments, the vaccine comprises a combination selected from the groups consisting of: one or more DNA vaccines, one or more recombinant vaccines, one or more protein subunit vaccines, one or more compositions comprising the immunogen, one or more attenuated vaccines and one or more killed vaccines.

According to some embodiments, a vaccine is delivered to an individual to modulate the activity of the individual's immune system and thereby enhance the immune response against HPV. When a nucleic acid molecule that encodes the protein is taken up by cells of the individual the nucleotide sequence is expressed in the cells and the protein are thereby delivered to the individual. Methods of delivering the coding sequences of the protein on nucleic acid molecule such as plasmid, as part of recombinant vaccines and as part of attenuated vaccines, as isolated proteins or proteins part of a vector are provided.

Compositions and methods are provided which prophylactically and/or therapeutically immunize an individual against HPV.

Compositions for delivering nucleic acid molecules that comprise a nucleotide sequence that encodes the immunogen are operably linked to regulatory elements. Compositions may include a plasmid that encodes the immunogen, a recombinant vaccine comprising a nucleotide sequence that encodes the immunogen, a live attenuated pathogen that encodes a protein of the invention and/or includes a protein of the invention; a killed pathogen includes a protein of the invention; or a composition such as a liposome or subunit vaccine that comprises a protein of the invention. The present invention further relates to injectable pharmaceutical compositions that comprise compositions.

SEQ ID NO:1 comprises a nucleotide sequence that encodes a consensus immunogen of HPV 18 E6 and E7 proteins. SEQ ID NO:5 includes SEQ ID NO:1 and further comprises an IgE leader sequence linked to the nucleotide sequence that encodes a consensus immunogen of HPV 18 E6 and E7 proteins. SEQ ID NO:2 comprises the amino acid sequence for the consensus immunogen of HPV 18 E6 and E7 proteins. SEQ ID NO:6 includes SEQ ID NO:2 and further comprises an IgE leader sequence linked to a consensus immunogen sequence. The IgE leader sequence is SEQ ID NO:4 and may be encoded by SEQ ID NO:3. SEQ ID NO:7 is the nucleic acid sequence of the plasmid pGX302 with SEQ ID NO:5 incorporated for expression therein.

In some embodiments, vaccines include SEQ ID NO:2, or a nucleic acid molecule that encodes SEQ ID NO:2. In some embodiments, vaccines include SEQ ID NO:1 as a nucleic acid molecule that encodes SEQ ID NO:2. In some embodiments, vaccines preferably comprise SEQ ID NO:6 or a nucleic acid molecule that encodes it. In some embodiments, vaccines preferably comprise SEQ ID NO:5 as a nucleic acid molecule that encodes SEQ ID NO:6. In some embodiments, vaccines preferably comprise SEQ ID NO:7.

Fragments of SEQ ID NO:1 may comprise 90 or more nucleotides. In some embodiments, fragments of SEQ ID NO:1 may comprise 180 or more nucleotides; in some embodiments, 270 or more nucleotides; in some embodiments 360 or more nucleotides; in some embodiments, 450 or more nucleotides; in some embodiments 540 or more nucleotides; in some embodiments, 630 or more nucleotides; in some embodiments, 720 or more nucleotides; and in some embodiments, 770 or more nucleotides. In some embodiments, fragments of SEQ ID NO:1 such as those set forth herein may further comprise coding sequences for the IgE leader sequences. In some embodiments, fragments of SEQ ID NO:1 do not comprise coding sequences for the IgE leader sequences. Fragments of SEQ ID NO:1 may comprise fewer than 180 nucleotides, in some embodiments fewer than 270 nucleotides, in some embodiments fewer than 360 nucleotides, in some embodiments fewer than 450 nucleotides, in some embodiments fewer than 540 nucleotides, in some embodiments fewer than 630 nucleotides, in some embodiments fewer than 690 nucleotides, in some embodiments fewer than 760 nucleotides, and in some embodiments fewer than 780 nucleotides.

Fragments of SEQ ID NO:2 may comprise 30 or more amino acids. In some embodiments, fragments of SEQ ID NO:2 may comprise 60 or more amino acids; in some embodiments, 90 or more amino acids; in some embodiments, 120 or more amino acids; in some embodiments; 150 or more amino acids; in some embodiments 180 or more amino acids; in some embodiments, 210 or more amino acids; and in some embodiments, 240 or more amino acids. Fragments may comprise fewer than 90 amino acids, in some embodiments fewer than 120 amino acids, in some embodiments fewer than 150 amino acids, in some embodiments fewer than 180 amino acids, in some embodiments fewer than 210 amino acids, and in some embodiments fewer than 240 amino acids.

All fragments of SEQ ID NO:5 comprise coding sequences encoding HPV sequences, i.e. the fragments of SEQ ID NO:5 must comprise sequences in addition to those encoding the IgE leader peptide. In some embodiments, fragments of SEQ ID NO:5 comprise 90 or more nucleotides. In some embodiments, fragments of SEQ ID NO:5 may comprise 180 or more nucleotides; in some embodiments, 270 or more nucleotides; in some embodiments 360 or more nucleotides; in some embodiments, 450 or more nucleotides; in some embodiments 540 or more nucleotides; in some embodiments, 630 or more nucleotides; in some embodiments, 720 or more nucleotides; in some embodiments, 810 or more nucleotides; and in some embodiments, 830 or more nucleotides. Fragments of SEQ ID NO:5 may comprise fewer than 180 nucleotides, in some embodiments fewer than 270 nucleotides, in some embodiments fewer than 360 nucleotides, in some embodiments fewer than 450 nucleotides, in some embodiments fewer than 540 nucleotides, in some embodiments fewer than 630 nucleotides, in some embodiments fewer than 690 nucleotides, in some embodiments fewer than 720 nucleotides, in some embodiments fewer than 780 nucleotides, and in some embodiments fewer than 840 nucleotides.

Fragments of SEQ ID NO:6 may comprise 30 or more amino acids including HPV sequences. In some embodiments, fragments of SEQ ID NO:6 may comprise 60 or more amino acids including HPV sequences; in some embodiments, 90 or more amino acids including HPV sequences; in some embodiments, 120 or more amino acids including HPV sequences; in some embodiments; 150 or more amino acids including HPV sequences; in some embodiments 180 or more amino acids including HPV sequences; in some embodiments, 210 or more amino acids including HPV sequences; in some embodiments, 240 or more amino acids including HPV sequences; and in some embodiments, 270 or more amino acids including HPV sequences. Fragments may comprise fewer than 90 amino acids including HPV sequences, in some embodiments fewer than 120 amino acids including HPV sequences, in some embodiments fewer than 150 amino acids including HPV sequences, in some embodiments fewer than 180 amino acids including HPV sequences, in some embodiments fewer than 210 amino acids including HPV sequences, in some embodiments fewer than 240 amino acids including HPV sequences, and in some embodiments fewer than 270 amino acids including HPV sequences.

According to some embodiments, methods of inducing an immune response in individuals against an immunogen comprise administering to the individual the amino acid sequence for the consensus immunogen of HPV 18 E6 and E7 proteins, or functional fragments thereof, or expressible coding sequences thereof. Some embodiments comprise an isolated nucleic acid molecule that encodes the amino acid sequence for the consensus immunogen of HPV 18 E6 and E7 proteins or a fragment thereof. Some embodiments comprise a recombinant vaccine that encodes the amino acid sequence for the consensus immunogen of HPV 18 E6 and E7 proteins or a fragment thereof. Some embodiments comprise a subunit vaccine that comprises the amino acid sequence for the consensus immunogen of HPV 18 E6 and E7 proteins or a fragment thereof. Some embodiments comprise a live attenuated vaccine and/or a killed vaccine that comprise the amino acid sequence for the consensus immunogen of HPV 18 E6 and E7 proteins.

Improved vaccines comprise proteins and genetic constructs that encode proteins with epitopes that make them particularly effective as immunogens against which anti-HPV immune responses can be induced. Accordingly, vaccines can be provided to induce a therapeutic or prophylactic immune response. In some embodiments, the means to deliver the immunogen is a DNA vaccine, a recombinant vaccine, a protein subunit vaccine, a composition comprising the immunogen, an attenuated vaccine or a killed vaccine. In some embodiments, the vaccine comprises a combination selected from the groups consisting of: one or more DNA vaccines, one or more recombinant vaccines, one or more protein subunit vaccines, one or more compositions comprising the immunogen, one or more attenuated vaccines and one or more killed vaccines.

Aspects of the invention provide methods of delivering the coding sequences of the protein on nucleic acid molecule such as plasmid, as part of recombinant vaccines and as part of attenuated vaccines, as isolated proteins or proteins part of a vector.

According to some aspects of the present invention, compositions and methods are provided which prophylactically and/or therapeutically immunize an individual DNA vaccines are described in U.S. Pat. Nos. 5,593,972, 5,739,118, 5,817,637, 5,830,876, 5,962,428, 5,981,505, 5,580,859, 5,703,055, 5,676,594, and the priority applications cited therein, which are each incorporated herein by reference. In addition to the delivery protocols described in those applications, alternative methods of delivering DNA are described in U.S. Pat. Nos. 4,945,050 and 5,036,006, which are both incorporated herein by reference.

The present invention relates to improved attenuated live vaccines, improved killed vaccines and improved vaccines that use recombinant vectors to deliver foreign genes that encode antigens and well as subunit and glycoprotein vaccines. Examples of attenuated live vaccines, those using recombinant vectors to deliver foreign antigens, subunit vaccines and glycoprotein vaccines are described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

When taken up by a cell, the genetic construct(s) may remain present in the cell as a. functioning extrachromosomal molecule and/or integrate into the cell's chromosomal DNA. DNA may be introduced into cells where it remains as separate genetic material in the form of a plasmid or plasmids. Alternatively, linear DNA that can integrate into the chromosome may be introduced into the cell. When introducing DNA into the cell, reagents that promote DNA integration into chromosomes may be added. DNA sequences that are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (MV) such as the BIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal that is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pVAX1, pCEP4 and pREP4 from Invitrogen (San Diego, Calif.) contain the Epstein Barr virus origin of replication and nuclear antigen EBNA-1 coding region which produces high copy episomal replication without integration.

In some preferred embodiments related to immunization applications, nucleic acid molecule(s) are delivered which include nucleotide sequences that encode protein of the invention, and, additionally, genes for proteins which further enhance the immune response against such target proteins. Examples of such genes are those which encode other cytokines and lymphokines such as alpha-interferon, gamma-interferon, platelet derived growth factor (PDGF), TNFα, TNFβ, GM-CSF, epidermal growth factor (EGF), IL-1, IL-2, IL-4, IL-5, IL-6, IL-10, IL-12, IL-18, MHC, CD80, CD86 and IL-15 including IL-15 having the signal sequence deleted and optionally including the signal peptide from IgE. Other genes which may be useful include those encoding: MCP-1, MIP-1α, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the genetic construct.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs that are functional in the cells.

In some embodiments, gene constructs may be provided in which the coding sequences for the proteins described herein are linked to IgE signal peptide. In some embodiments, proteins described herein are linked to IgE signal peptide.

In some embodiments for which protein is used, for example, one having ordinary skill in the art can, using well known techniques, produce and isolate proteins of the invention using well known techniques. In some embodiments for which protein is used, for example, one having ordinary skill in the art can, using well known techniques, inserts DNA molecules that encode a protein of the invention into a commercially available expression vector for use in well known expression systems. For example, the commercially available plasmid pSE420 (Invitrogen, San Diego, Calif.) may be used for production of protein in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I or pcDNA3 (Invitrogen, San Diego, Calif.) may, for example, be used for production in mammalian cells such as Chinese Hamster Ovary cells. One having ordinary skill in the art can use these commercial expression vectors and systems or others to produce protein by routine techniques and readily available starting materials. (See e.g., Sambrook et al., Molecular Cloning a Laboratory Manual, Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers are readily available and known in the art for a variety of hosts. See e.g., Sambrook et al., Molecular Cloning a Laboratory Manual, Second Ed. Cold Spring Harbor Press (1989). Genetic constructs include the protein coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes protein of the invention from readily available starting materials. The expression vector including the DNA that encodes the protein is used to transform the compatible host which is then cultured and maintained under conditions wherein expression of the foreign DNA takes place.

The protein produced is recovered from the culture, either by lysing the cells or from the culture medium as appropriate and known to those in the art. One having ordinary skill in the art can, using well known techniques, isolate protein that is produced using such expression systems. The methods of purifying protein from natural sources using antibodies which specifically bind to a specific protein as described above may be equally applied to purifying protein produced by recombinant DNA methodology.

In addition to producing proteins by recombinant techniques, automated peptide synthesizers may also be employed to produce isolated, essentially pure protein. Such techniques are well known to those having ordinary skill in the art and are useful if derivatives which have substitutions not provided for in DNA-encoded protein production.

The nucleic acid molecules may be delivered using any of several well known technologies including DNA injection (also referred to as DNA vaccination), recombinant vectors such as recombinant adenovirus, recombinant adenovirus associated virus and recombinant vaccinia.

Routes of administration include, but are not limited to, intramuscular, intransally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include intramuscular, intraperitoneal, intradermal and subcutaneous injection. Genetic constructs may be administered by means including, but not limited to, electroporation methods and devices, traditional syringes, needleless injection devices, or "microprojectile bombardment gone guns".

Examples of electroporation devices and electroporation methods preferred for facilitating delivery of the DNA vaccines, include those described in U.S. Pat. No. 7,245,963 by Draghia-Akli, et al., U.S. Patent Pub. 2005/0052630 submitted by Smith, et al., the contents of which are hereby incorporated by reference in their entirety. Also preferred, are electroporation devices and electroporation methods for facilitating delivery of the DNA vaccines provided in co-pending and co-owned U.S. patent application Ser. No. 11/874,072, filed Oct. 17, 2007, which claims the benefit under 35 USC 119(e) to U.S. Provisional Application Ser. Nos. 60/852,149, filed Oct. 17, 2006, and 60/978,982, filed Oct. 10, 2007, all of which are hereby incorporated in their entirety.

The following is an example of an embodiment using electroporation technology, and is discussed in more detail in the patent references discussed above: electroporation devices can be configured to deliver to a desired tissue of a mammal a pulse of energy producing a constant current similar to a preset current input by a user. The electroporation device comprises an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation component can function as one element of the electroporation devices, and the other elements are separate elements (or components) in communication with the electroporation component. In some embodiments, the electroporation component can function as more than one element of the electroporation devices, which can be in communication with still other elements of the electroporation devices separate from the electroporation component. The use of electroporation technology to deliver the improved HCV vaccine is not limited by the elements of the electroporation devices existing as parts of one electromechanical or mechanical device, as the elements can function as one device or as separate elements in communication with one another. The electroporation component is capable of delivering the pulse of energy that produces the constant current in the desired tissue, and includes a feedback mechanism. The electrode assembly includes an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism can receive the measured impedance and can adjust the pulse of energy delivered by the electroporation component to maintain the constant current.

In some embodiments, the plurality of electrodes can deliver the pulse of energy in a decentralized pattern. In some embodiments, the plurality of electrodes can deliver the pulse of energy in the decentralized pattern through the control of the electrodes under a programmed sequence, and the programmed sequence is input by a user to the electroporation component. In some embodiments, the programmed sequence comprises a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

In some embodiments, the feedback mechanism is performed by either hardware or software. Preferably, the feedback mechanism is performed by an analog closed-loop circuit. Preferably, this feedback occurs every 50 µs, 20 µs, 10 µs or 1 µs, but is preferably a real-time feedback or instantaneous (i.e., substantially instantaneous as determined by available techniques for determining response time). In some embodiments, the neutral electrode measures the impedance in the desired tissue and communicates the impedance to the feedback mechanism, and the feedback mechanism responds to the impedance and adjusts the pulse of energy to maintain the constant current at a value similar to the preset current. In some embodiments, the feedback mechanism maintains the constant current continuously and instantaneously during the delivery of the pulse of energy.

In some embodiments, the nucleic acid molecule is delivered to the cells in conjunction with administration of a polynucleotide function enhancer or a genetic vaccine facilitator agent. Polynucleotide function enhancers are described in U.S. Pat. Nos. 5,593,972, 5,962,428 and International Application Serial Number PCT/US94/00899 filed Jan. 26, 1994, which are each incorporated herein by reference. Genetic vaccine facilitator agents are described in U.S. Ser. No. 021, 579 filed Apr. 1, 1994, which is incorporated herein by reference. The co-agents that are administered in conjunction with nucleic acid molecules may be administered as a mixture with the nucleic acid molecule or administered separately simultaneously, before or after administration of nucleic acid molecules. In addition, other agents which may function transfecting agents and/or replicating agents and/or inflammatory agents and which may be co-administered with a GVF include growth factors, cytokines and lymphokines such as α-interferon, gamma-interferon, GM-CSF, platelet derived growth factor (PDGF), TNF, epidermal growth factor (EGF), IL-1, IL-2, IL-4, IL-6, IL-10, IL-12 and IL-15 as well as fibroblast growth factor, surface active agents such as immune-stimulating complexes (ISCOMS), Freunds incomplete adjuvant, LPS analog including monophosphoryl Lipid A (WL), muramyl peptides, quinone analogs and vesicles such as squalene and squalene, and hyaluronic acid may also be used administered in conjunction with the genetic construct In some embodiments, an immunomodulating protein may be used as a GVF. In some embodiments, the nucleic acid molecule is provided in association with PLG to enhance delivery/uptake.

The pharmaceutical compositions according to the present invention comprise about 1 nanogram to about 2000 micrograms of DNA. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

According to some embodiments of the invention, methods of inducing immune responses are provided. The vaccine may be a protein based, live attenuated vaccine, a cell vaccine, a recombinant vaccine or a nucleic acid or DNA vaccine. In some embodiments, methods of inducing an immune response in individuals against an immunogen, including methods of inducing mucosal immune responses, comprise administering to the individual one or more of CTACK protein, TECK protein, MEC protein and functional fragments thereof or expressible coding sequences thereof in combination with an isolated nucleic acid molecule that encodes protein of the invention and/or a recombinant vaccine that encodes protein of the invention and/or a subunit vaccine that protein of the invention and/or a live attenuated vaccine and/or a killed vaccine. The one or more of CTACK protein, TECK protein, MEC protein and functional fragments thereof may be administered prior to, simultaneously with or after administration of the isolated nucleic acid molecule that encodes an immunogen; and/or recombinant vaccine that encodes an immunogen and/or subunit vaccine that comprises an immunogen and/or live attenuated vaccine and/or killed vaccine. In some embodiments, an isolated nucleic acid molecule that encodes one or more proteins of selected from the group consisting of: CTACK, TECK, MEC and functional fragments thereof is administered to the individual.

The present invention is further illustrated in the following Example. It should be understood that this Example, while indicating embodiments of the invention, is given by way of illustration only. From the above discussion and this Example, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Each of the U.S. patents, U.S. applications, and references cited throughout this disclosure are hereby incorporated in their entirety by reference.

EXAMPLE

Figure 1:
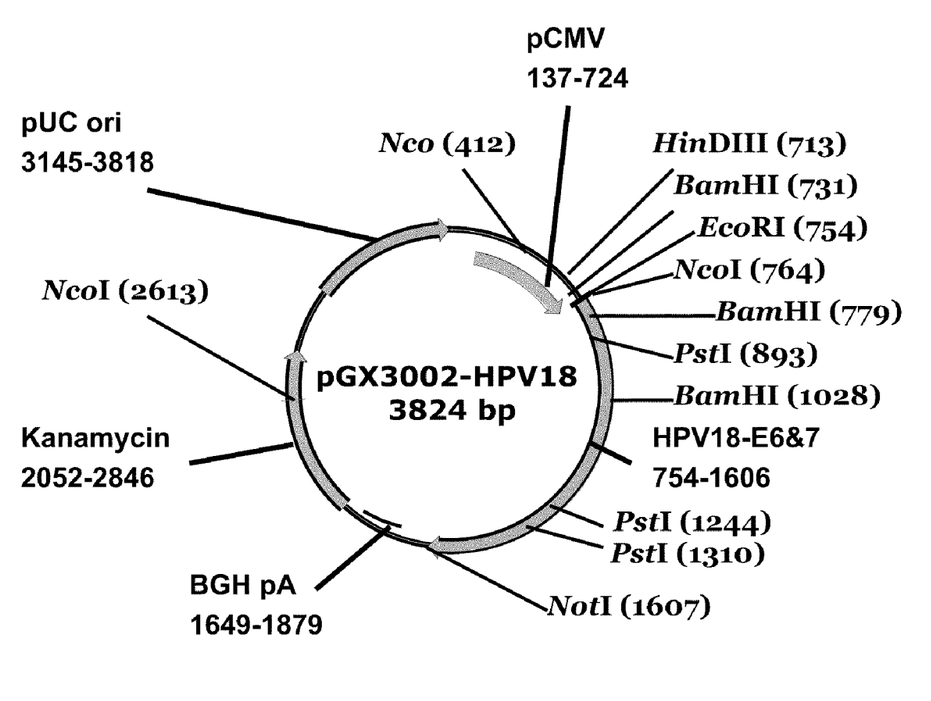
FIG. 1 provides a description of the plasmid construct.

An optimized consensus sequences for human papilloma virus (HPV) viral proteins 18 E6&7 was prepared. The sequence is designed for high levels of expression. This sequence is useful in our genetic immunization technology. Results from experiments performed using the consensus sequence were positive. FIG. 1 provides a description of the plasmid construct which includes the nucleic acid sequence of the consensus HPV 18-6&7 in plasmid pGX3002 (SEQ ID NO:7). The nucleic acid sequence of the consensus HPV 18-6&7 that is incorporated into plasmid pGX3002 includes coding sequence for the IgE leader peptide linked to the coding sequences of the consensus HPV 18-6&7.

Plasmid pGX3002 expresses the optimized human papilloma virus 18-6&7 antigens (HPV 18 E6&7), driven by the CMV promoter (pCMV) with the bovine growth hormone 3' end and poly-adenylation signal (bGHpA) using a pVAX backbone that includes—the kanamycin resistance gene (Kan) and plasmid origin of replication (pUC ori).

| Elements: | Base Pairs |
| --- | --- |
| CMV Promoter: | 137-724 |
| HPV 18-6&7 Coding Sequence: | 754-1606 |
| bGH PolyA: | 1649-1879 |
| Kan Resistance: | 2052-2846 |
| pUC Ori: | 3145-3818 |

The invention claimed is:

1. An isolated nucleic acid molecule comprising a nucleotide sequence selected from the group consisting of:
SEQ ID NO:1;
fragments of at least 630 nucleotides of SEQ ID NO: 1; and
sequences having at least 95% homology to SEQ ID NO: 1.

2. The nucleic acid molecule of claim 1, wherein the nucleic acid molecule comprises SEQ ID NO:1.

3. The nucleic acid molecule of claim 1, wherein the nucleic acid molecule comprises a sequence having at least 95% homology to SEQ ID NO:1.

4. The nucleic acid molecule of claim 1, wherein the nucleic acid molecule comprises a sequence having at least 98% homology to SEQ ID NO:1.

5. The nucleic acid molecule of claim 1, wherein the nucleic acid molecule comprises a sequence having at least 99% homology to SEQ ID NO:1.

6. An isolated nucleic acid molecule comprising a nucleotide sequence selected from the group consisting of:
nucleotide sequences that encode SEQ ID NO:2;
nucleotide sequences that encode an amino acid sequences having at least 95% homology to SEQ ID NO:2; and
fragments of nucleotide sequences that encode SEQ ID NO:2 having at least 630 nucleotides of nucleotide sequences that encode SEQ ID NO:2.

7. The nucleic acid molecule of claim 6 comprising a nucleotide sequence that encodes SEQ ID NO:2.

8. The nucleic acid molecule of claim 1 wherein said molecule is a plasmid.

9. A composition comprising a nucleic acid molecule of claim 1.

10. An injectable composition comprising a nucleic acid molecule of claim 1.

11. A method of inducing an immune response in an individual against HPV comprising administering to said individual a composition comprising a nucleic acid molecule of claim 1.

12. The method of claim 11 wherein said nucleic acid molecule is a DNA molecule.

13. The method of claim 12 wherein said nucleic acid molecule is a plasmid.

14. The method of claim 11 wherein said nucleic acid molecule is administered to the individual by electroporation.

15. The nucleic acid molecule of claim 6, wherein the nucleotide sequence encodes a protein that comprises a sequence having at least 95% homology to SEQ ID NO:2.

16. The nucleic acid molecule of claim 6, wherein the nucleotide sequence encodes a protein that comprises a sequence having at least 98% homology to SEQ ID NO:2.

17. The nucleic acid molecule of claim 6, wherein the nucleotide sequence encodes a protein that comprises a sequence having at least 99% homology to SEQ ID NO:2.

18. The nucleic acid molecule of claim 6 wherein said molecule is a plasmid.

19. A composition comprising a nucleic acid molecule of claim 6.

20. An injectable composition comprising a nucleic acid molecule of claim 6.

21. A method of inducing an immune response in an individual against HPV comprising administering to said individual a composition comprising a nucleic acid molecule of claim 6.

22. The method of claim 21 wherein said nucleic acid molecule is a DNA molecule.

23. The method of claim 22 wherein said nucleic acid molecule is a plasmid.

24. The method of claim 21 wherein said nucleic acid molecule is administered to the individual by electroporation.

25. The nucleic acid molecule of claim 6 further comprising an IgE leader nucleotide sequence.

26. The nucleic acid molecule of claim 6, wherein said fragments comprise at least 720 nucleotides.

27. The nucleic acid molecule of claim 6, wherein said fragments comprise at least 770 nucleotides.

28. The nucleic acid molecule of claim 1 further comprising an IgE leader nucleotide sequence.

29. The nucleic acid molecule of claim 1, wherein said fragments of nucleotide sequences comprises at least 720 nucleotides.

30. The nucleic acid molecule of claim 1, wherein said fragments of nucleotide sequences comprises at least 770 nucleotides.

31. The nucleic acid molecule of claim 1 comprising a nucleotide sequence selected from the group consisting of:
SEQ ID NO:1;
fragments of at least 720 nucleotides of SEQ ID NO:1; and
sequences having at least 98% homology to SEQ ID NO:1.

32. The nucleic acid molecule of claim 1 comprising a nucleotide sequence selected from the group consisting of:
SEQ ID NO:1;
fragments of at least 770 nucleotides of SEQ ID NO:1; and
sequences having at least 99% homology to SEQ ID NO:1.

33. The nucleic acid molecule of claim 6 comprising a nucleotide sequence selected from the group consisting of:
nucleotide sequences that encode SEQ ID NO:2;
nucleotide sequences that encode amino acid sequences having at least 98% homology to SEQ ID NO:2; and
fragments of nucleotide sequences that encode SEQ ID NO:2 having at least 720 nucleotides of nucleotide sequences that encode SEQ ID NO:2.

34. The nucleic acid molecule of claim 6 comprising a nucleotide sequence selected from the group consisting of:
nucleotide sequences that encode SEQ ID NO:2;
nucleotide sequences that encode amino acid sequences having at least 99% homology to SEQ ID NO:2; and
fragments of nucleotide sequences that encode SEQ ID NO:2 having at least 770 nucleotides of nucleotide sequences that encode SEQ ID NO:2.

35. The method of claim 11 wherein said nucleic acid molecule comprising a nucleotide sequence selected from the group consisting of:
SEQ ID NO:1;
fragments of at least 720 nucleotides of SEQ ID NO:1; and
sequences having at least 98% homology to SEQ ID NO:1.

36. The method of claim 11 wherein said nucleic acid molecule comprising a nucleotide sequence selected from the group consisting of:
SEQ ID NO:1;
fragments of at least 770 nucleotides of SEQ ID NO:1; and
sequences having at least 99% homology to SEQ ID NO:1.

37. The method of claim 11 wherein said nucleic acid molecule comprises SEQ ID NO:1.

38. The method of claim 21 wherein said nucleic acid molecule comprising a nucleotide sequence selected from the group consisting of: nucleotide sequences that encode SEQ ID NO:2;
nucleotide sequences that encode amino acid sequences having at least 98% homology to SEQ ID NO:2; and
fragments of nucleotide sequences that encode SEQ ID NO:2 having at least 720 nucleotides of nucleotide sequences that encode SEQ ID NO:2.

39. The method of claim 21 wherein said nucleic acid molecule comprising a nucleotide sequence selected from the group consisting of:
nucleotide sequences that encode SEQ ID NO:2;
nucleotide sequences that encode amino acid sequences having at least 99% homology to SEQ ID NO:2; and
fragments of nucleotide sequences that encode SEQ ID NO:2 having at least 770 nucleotides of nucleotide sequences that encode SEQ ID NO:2.

40. The method of claim 21 wherein said nucleic acid molecule comprises a nucleotide sequence that encodes SEQ ID NO:2.

* * * * *